United States Patent
Beebe et al.

(10) Patent No.: US 9,867,974 B2
(45) Date of Patent: Jan. 16, 2018

(54) MICROFLUIDIC DEVICE FOR MULTIPLEXED POINT SOURCE ADMINISTRATION OF COMPOUNDS

(71) Applicant: Wisconsin Alumni Research Foundation, Madison, WI (US)

(72) Inventors: David J. Beebe, Monona, WI (US); Mark E. Burkard, Cross Plains, WI (US); Jay W. Warrick, Madison, WI (US); David J Guckenberger, Oconomowoc, WI (US); Lee G. Wilke, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 157 days.

(21) Appl. No.: 14/727,399

(22) Filed: Jun. 1, 2015

(65) Prior Publication Data

US 2016/0346524 A1    Dec. 1, 2016

(51) Int. Cl.
*A61M 31/00*    (2006.01)
*A61M 37/00*    (2006.01)

(52) U.S. Cl.
CPC .............................. *A61M 37/0069* (2013.01)

(58) Field of Classification Search
CPC ........ A61B 2090/3908; A61B 10/0233; A61B 5/0084; A61B 10/02; A61B 17/3468; A61B 17/3478; A61B 1/041; A61M 31/002; A61M 5/14276; A61M 37/0069; A61M 2205/04; A61M 31/00; A61M 5/1452; A61K 9/0004; A61K 9/0024
USPC ..... 600/432; 604/21, 272, 506, 891.1, 892.1
See application file for complete search history.

(56) References Cited

U.S. PATENT DOCUMENTS

| | | | |
|---|---|---|---|
| 5,067,952 A * | 11/1991 | Gudov .................. | A61N 1/406 600/10 |
| 5,542,935 A * | 8/1996 | Unger ................... | A61K 9/127 424/450 |
| 5,704,910 A * | 1/1998 | Humes ...................... | A61F 2/01 604/502 |
| 5,715,824 A * | 2/1998 | Unger ................... | A61K 9/127 264/4.1 |
| 8,834,428 B2 | 9/2014 | Bahrami et al. | |

(Continued)

OTHER PUBLICATIONS http://presagebio.com/our-platform-video, Jan. 16, 2015.
(Continued)

*Primary Examiner* — Gerald Landry, II
(74) *Attorney, Agent, or Firm* — Boyle Fredrickson, S.C.

(57) ABSTRACT

A device is provided for the administration of a compound in a body. The device includes a capsule having a reservoir therein for receiving the compound therein and a delivery instrument for positioning the capsule within the body. The delivery instrument includes a barrel having an interior adapted to receive the capsule therein and a dispersal element interacting with the barrel to selectively expel the capsule therefrom and into the body. A diffusion regulator communicates with the reservoir and controls the diffusion of the compound from the reservoir into the body. A retention structure projects from capsule and is configured to retain the capsule at a desired location within the body. Multiple devices may be used in conjunction to provide a multiplexed point source to administer multiple compounds simultaneously in vivo.

20 Claims, 3 Drawing Sheets

(56) References Cited

U.S. PATENT DOCUMENTS

| | | | | |
|---|---|---|---|---|
| 2002/0090388 | A1* | 7/2002 | Humes | A61K 9/0019 424/422 |
| 2003/0064095 | A1* | 4/2003 | Martin | A61K 9/0004 424/451 |
| 2004/0034357 | A1* | 2/2004 | Beane | A61L 31/16 606/232 |
| 2004/0068157 | A1* | 4/2004 | Gellman | A61N 1/406 600/4 |
| 2005/0152949 | A1* | 7/2005 | Hotchkiss | A61K 9/0024 424/423 |
| 2006/0106361 | A1* | 5/2006 | Muni | A61B 5/06 604/500 |
| 2006/0259006 | A1* | 11/2006 | McKay | A61B 17/3478 604/506 |
| 2007/0243225 | A1* | 10/2007 | McKay | A61K 9/0024 424/423 |
| 2008/0300571 | A1* | 12/2008 | LePivert | A61B 18/1492 604/503 |
| 2009/0202608 | A1* | 8/2009 | Alessi | A61K 9/0004 424/424 |
| 2009/0240140 | A1* | 9/2009 | Fitelzon | A61B 90/39 600/426 |
| 2009/0246126 | A1* | 10/2009 | Shani | A61N 5/1001 424/1.29 |
| 2010/0262001 | A1* | 10/2010 | Morris | A61M 25/0084 600/424 |
| 2011/0263922 | A1* | 10/2011 | Dornberger | A61B 5/0071 600/3 |
| 2012/0041393 | A1* | 2/2012 | Ahmann | A61B 17/7097 604/272 |
| 2012/0059349 | A1* | 3/2012 | Kuo | A61M 5/1407 604/500 |
| 2012/0259268 | A1* | 10/2012 | Gerrans | A61K 41/00 604/21 |
| 2015/0064241 | A1* | 3/2015 | Conrad | A61B 5/0071 424/451 |
| 2015/0126968 | A1* | 5/2015 | Abhishek | A61M 31/002 604/514 |
| 2016/0074626 | A1* | 3/2016 | Weadock | A61M 25/0169 600/3 |
| 2016/0256611 | A1* | 9/2016 | Fitz | A61L 31/10 |
| 2016/0279399 | A1* | 9/2016 | Lee | A61K 9/0004 |

OTHER PUBLICATIONS

Jonas et al., "An implantable microdevice to perform high-throughput in vivo drug sensitivity testing in tumors", www.ScienceTranslationalMedicine.org, vol. 7, Issue 284, Apr. 22, 2015, 13 pages.

Klinghoffer et al., "A technology pattern to assess multiple cancer agents simultaneously within a patient's tumor", www.ScienceTranslationalMedicine.org, vol. 7, Issue 284, Apr. 22, 2015, 14 pages.

* cited by examiner

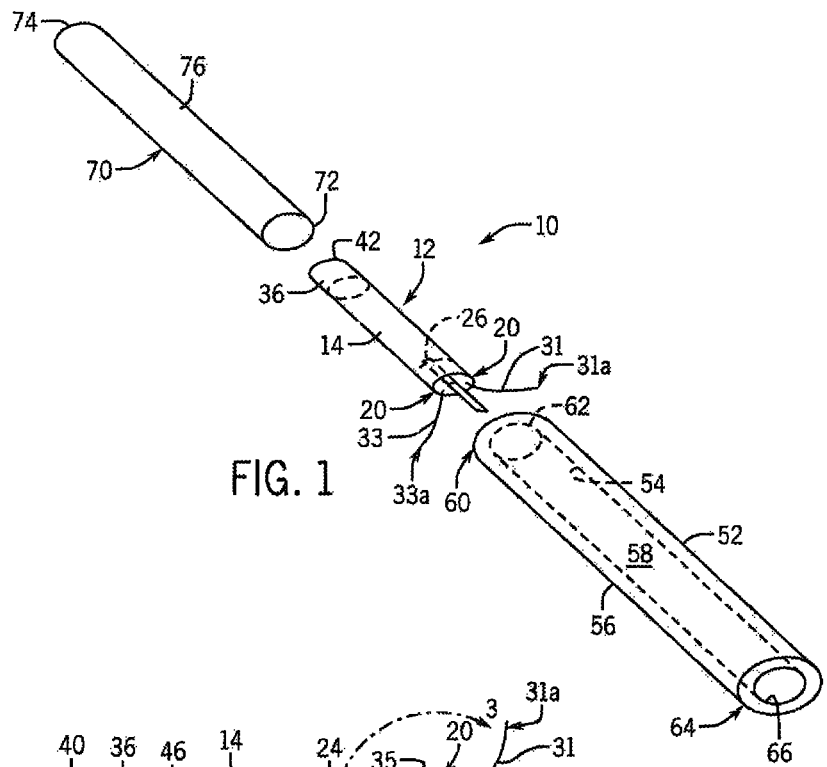
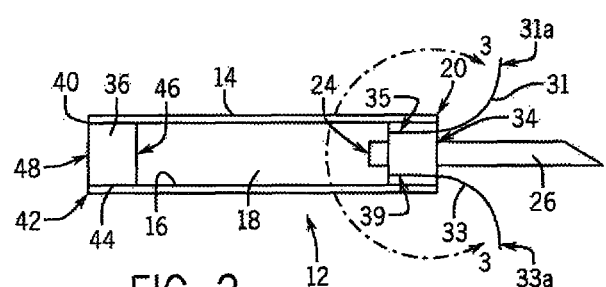
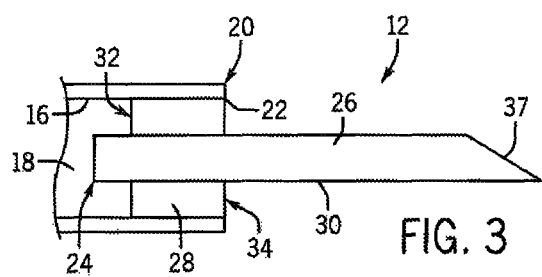

MICROFLUIDIC DEVICE FOR MULTIPLEXED POINT SOURCE ADMINISTRATION OF COMPOUNDS

REFERENCE TO GOVERNMENT GRANT

This invention was made with government support under CA014520 awarded by the National institutes of Health. The government has certain rights in the invention.

FIELD OF THE INVENTION

This invention relates generally to microfluidic devices, and in particular, to a microfluidic device that may be used to provide for the multiplexed point source administration of compounds in vivo.

BACKGROUND AND SUMMARY OF THE INVENTION

Genomic profiling of tumors suggests that each cancer is genetically unique and future success in treatment will require highly individualized selection of therapy. However, the process of matching effective drugs to cancer genotypes is an inherently inefficient process. Typically, each drug is tested on a population of 50-200 patients having the matching genomic characteristics. However, many characteristics are rare, occurring in only a small fraction of patients, and some may be unique, when considering all the possible genetic modifiers. These considerations can make studies of these patient cohorts inefficient or impractical. One potential alternative is in vitro drug sensitivity testing where multiple drugs can be tested against each cancer. Unfortunately, in vitro drug sensitivity assays for cancer have been unsuccessful despite decades of effort. Simultaneous testing of many drugs in vivo on each patient would overcome significant barriers to the rapid and efficient development of effective drugs for individualized therapy.

A further barrier to individualized treatments is the problem of predicting sensitivity to existing treatments, which (though toxic) are effective in only a fraction of patients. One precedent for this approach is in bacterial sensitivity testing. In the 1950's Kirby and Bauer developed a method to test bacterial sensitivity to antibiotics. This simple and elegant test allows for the selection of specific and effective antibiotic therapies for each patient and is in routine clinical use today. Analogously, this process could be applied to cancer. Utilizing multiplexed drug delivery at the site of the cancer in cancer patients would allow for the identification of effective therapies, while sparing patients the toxicity of systemic administration of ineffective therapies. Unfortunately, the in vitro analog to the Kirby-Bauer test in cancer has not predicted benefit to chemotherapy, possibly due to the variability in which particular cancer cell clone grows in the lab or due to complex interactions between tumor cells and their environment within the human host.

As is known, current testing techniques are conducted in vitro despite the known importance of the tumor environment. By way of example, it is known that certain types of cancer cells, e.g. breast cancer cells, do not develop and metastasize without support from the local microenvironment. As such, it can be appreciated that the systemic use of in vitro testing (i.e. in the absence of an intact local microenvironment) likely prevents researchers from obtaining a complete understanding of a cancer's growth potential. Furthermore, in vivo, local tumor responses often predict the benefit of systemic therapy. Hence, it is highly desirable to provide a device which allows for the multiplexed point source administration of chemotherapeutic compounds in vivo.

Therefore, it is a primary object and feature of the present invention to provide a microfluidic device which may be used in the multiplexed point source administration of compounds (e.g. therapeutic, chemotherapeutic and anticancer compounds) in vivo.

It is a further object and feature of the present invention to provide a microfluidic device which may be used in the multiplexed point source administration of compounds that allows for the identification of effective therapies, while sparing patients the toxicity of systemic administration of ineffective therapies.

It is a still further object and feature of the present invention to provide a microfluidic device which may be used in the multiplexed point source administration of compounds that improves patient outcomes through more effective therapeutic decision making and accelerates the process of targeted drug development.

It is a still farther object and feature of the present invention to provide a microfluidic device which may be used in the multiplexed point source administration of compounds that is simple to utilize and inexpensive to manufacture.

It is a still further object and feature of the present invention to provide a microfluidic device which may be used in conjunction with other microfluidic devices to provide a multiplexed point source to administer multiple compounds simultaneously in vivo.

It is a still further object and feature of the present invention to provide a microfluidic device which may be installed within a human body, without any part protruding through the skin, to deliver a drug or a compound to a specific location over a period of days to weeks.

In accordance with the present invention, a device for the administration of a compound in a body is provided. The device includes a capsule having an inner surface defining a reservoir for receiving the compound therein. A diffusion regulator communicates with the reservoir. The diffusion regulator controls the diffusion of the compound from the reservoir into the body.

The capsule has opposite first and second ends. A seal is engageable with the first end of the capsule. The seal is configured for preventing the compound from exiting the reservoir through the first end of the capsule. The diffusion regulator includes a needle having a first end communicating with the reservoir and a second end receivable in the body. A retention structure projects from capsule. The retention structure is configured to retain the capsule at a desired location within the body. The retention structure may include at least one barb projecting from the second end of the capsule. The at least one barb is engageable with the body.

A delivery instrument is provided for positioning the capsule within the body. The delivery instrument includes a barrel, e.g. an elongated tube, having an inner surface defining a passage for receiving the capsule therein. A dispersal element, e.g. push rod, acts to expel the capsule from the barrel and into the body. For example, the push rod may be slideably received in a first end of the elongated tube. The push rod is engageable with the capsule for urging the capsule from the passage of the elongated tube through the second end thereof. A second end of the elongated tube may be beveled to facilitate the insertion of the elongated tube into the body.

In accordance with a further aspect of the present invention, a device is provided for the administration of a compound in a body. The device includes a capsule having a reservoir therein for receiving the compound therein. A delivery instrument is configured for positioning the capsule within the body. The delivery instrument includes a barrel having an interior adapted to receive the capsule therein. A dispersal element interacts with the capsule to selectively expel the capsule from barrel and into the body. A diffusion regulator communicates with the reservoir. The diffusion regulator controls the diffusion of the compound from the reservoir into the body. A retention structure projects from capsule. The retention structure is configured to retain the capsule at a desired location within the body.

The capsule has opposite first and second ends. A seal is engageable with the first end of the capsule. The seal is configured to prevent the compound from exiting the reservoir through the first end of the capsule. The diffusion regulator includes a needle having a first end communicating with the reservoir and a second end receivable in the body. The retention structure includes at least one barb projecting from the capsule. The at least one barb is movable from a first retracted position to a second extended position in response to the capsule being expelled from the barrel. The barrel may be defined by an elongated tube having an inner surface defining a passage for receiving the capsule therein. The dispersal element may include a push rod slideably received in the first end of the elongated tube. The push rod is engageable with the capsule for selectively urging the capsule from the passage of the elongated tube through the second end thereof. The second end of the elongated tube may be beveled to facilitate the insertion of the elongated tube into the body.

In accordance with a still further aspect of the present invention, a device is provided for the administration of a compound in a body. The device includes a capsule having a reservoir therein for receiving the compound therein. A diffusion regulator communicates with the reservoir. The diffusion regulator controls the diffusion of the compound from the reservoir into the body. A retention structure projects from capsule. The retention structure is configured to retain the capsule at a desired location within the body.

The capsule has opposite first and second ends. A seal is engageable with the first end of the capsule. The seal is configured to prevent the compound from exiting the reservoir through the first end of the capsule. The diffusion regulator includes a needle having a first end communicating with the reservoir and a second end receivable in the body. An injection structure is provided for injecting the capsule into the body. The retention structure includes at least one barb projecting from the capsule. The at least one barb is movable from a first retracted position to a second extended position in response to the capsule being injected into the body. The injection structure includes an elongated tube having an inner surface defining a passage for receiving the capsule therein. The injection structure further includes a push rod slideably received in the first end of the elongated tube. The push rod is engageable with the capsule for selectively urging the capsule from the passage of the elongated tube into the body through the second end thereof. The second end of the elongated tube may be beveled to facilitate the insertion of the elongated tube into the body.

BRIEF DESCRIPTION OF THE DRAWINGS

The drawings furnished herewith illustrate a preferred construction of the present invention in which the above advantages and features are clearly disclosed as well as other which will be readily understood from the following description of the illustrated embodiment.

In the drawings:

FIG. 1 is an exploded, isometric view of a microfluidic device in accordance with the present invention;

FIG. 2 is a schematic cross-sectional view of a capsule of the microfluidic device of FIG. 1;

FIG. 3 is an enlarged, schematic cross-sectional view of a capsule of the microfluidic device of the present invention, taken along line 3-3 of FIG. 2;

DETAILED DESCRIPTION OF THE DRAWINGS

Figure 4:
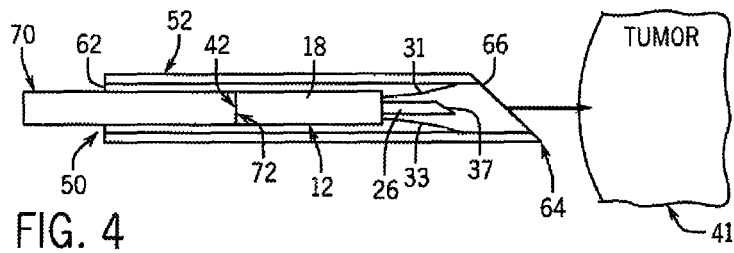
FIG. 4 is an enlarged, cross-sectional view of the microfluidic device of the present invention prior to insertion into a tumor.
Figure 5:
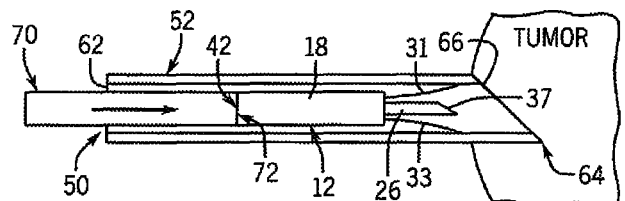
FIG. 5 is an enlarged, cross-sectional view showing insertion of a delivery instrument of the microfluidic device of the present invention into the tumor.
Figure 6:
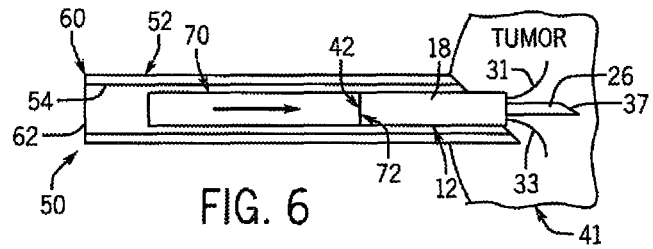
FIG. 6 is an enlarged, cross-sectional view showing insertion of the capsule of the microfluidic device into the tumor after insertion of the delivery instrument of the microfluidic device into the tumor.

Referring to FIG. 1, a microfluidic device that may be used to provide for the multiplexed point source administration of drugs, such as therapeutic, anticancer or chemotherapeutic compounds, in vivo is generally designated by the reference numeral 10. Microfluidic device 10 includes capsule 12 having generally cylindrical outer surface 14. In the depicted embodiment, inner surface 16 of capsule 12 is also generally cylindrical and defines reservoir 18, FIG. 2. It can be appreciated that reservoir 18 may have other configurations without deviating from the scope of the present invention.

Referring to FIGS. 2-3, first end 20 of capsule 12 defines a generally circular opening 22 adapted for receiving input end 24 of delivery needle 26. More specifically, input end 24 of delivery needle 26 is inserted through opening 22 in capsule 12 and retained in position in any conventional manner. For example, it is contemplated for sealer 28 to extend between outer surface 30 of delivery needle 26 and inner surface 16 of capsule 12 to form a fluid-tight seal between outer surface 30 of delivery needle 26 and inner surface 16 of capsule 12. Sealer 28 has a first end 32 spaced from input end 24 of delivery needle 26 so as to allow input end 24 of delivery needle 26 to communicate with reservoir 18.

As best seen in FIG. 2, second end 34 of sealer 28 is substantially flush with the first end 20 of capsule 12 and includes first and second barbs 31 and 33, respectively, projecting therefrom. Inner ends 35 and 39 of first and second barbs 31 and 33, is respectively, are seated within and captured by sealer 28. First and second barbs 31 and 33, respectively, are circumferentially spaced about outer surface 30 of delivery needle 26 and extend from second end 34 of sealer 28 at locations radially spaced from delivery needle 26. It is contemplated for first and second barbs 31 and 33, respectively, to be resilient, and have generally arcuate configurations such that first and second barbs 31 and 33, respectively, diverge from each other and from delivery needle 26. Output end 37 of delivery needle 26 is spaced from second end 34 of sealer 28, and hence first end of capsule 20. Output end 37 of delivery needle 26 may be beveled to facilitate insertion of delivery needle 26 into a desired portion of a body, such as a tumor 41 or the like, FIGS. 4-8.

For reasons hereinafter described, it is contemplated for reservoir 18 to receive a drug, compound or the like therein for insertion into a desired portion of body. By way of example, reservoir 18 receives a user selected compound therein. As best seen in FIG. 2, once the reservoir 18 is filled with the user selected compound, seal 36 is inserted into opening 40 in second end 42 of capsule 12. More specifically, outer surface 44 of seal 36 engages inner surface 16 of capsule 12 at a location adjacent second end 42 of capsule 12 so as provide a fluid-tight seal therebetween. Seal 36 has a first end 46 communicating with reservoir 18 and the user selected compound therein. Second end 48 of seal 36 is substantially flush with second end 42 of capsule 12.

Referring to FIGS. 1 and 4-7, microfluidic device 10 further includes injection structure or delivery instrument 50 for injecting capsule 12 into a desired portion of a body, such as a tumor 41 or the like. Delivery instrument 50 includes elongated tube 52 having inner and outer surfaces 54 and 56, respectively. Inner surface 54 of elongated to tube 52 defines passage 58 for receiving capsule 12 therein. Elongated tube 52 further includes a first end 60 defining an opening 62 in communication with passage 58. Second end 64 of elongated tube 52 defines output opening 66 which is in communication with passage 58. It is contemplated for second end 64 of elongated tube 52 to be beveled to facilitate the insertion of elongated tube 52 into a body.

Delivery instrument 50 further includes push rod 70 slideably received in opening 62 in first end 60 of elongated tube 52. In the depicted embodiment, push rod 70 is generally cylindrical is shape and has first and second opposite ends 72 and 74, respectively. With first end 72 of push rod 70 inserted through opening 62 in first end 60 of elongated tube 52, outer surface 76 of push rod 70 forms a slidable interface with inner surface 54 of elongated tube 52. As hereinafter described, it is intended for first end 72 of push rod 70 to engage second end 42 of capsule 12 to urge capsule 12 from the passage 58 of elongated tube 52 through output opening 66 thereof and into a desired portion of a body, such as a tumor 41.

In operation, reservoir 18 of capsule 12 is filled with the user selected compound, as previously described. Once the reservoir 18 is filled with the user selected compound, seal 36 is inserted into opening 40 in second end 42 of capsule 12. Thereafter, capsule 12 axially inserted into passage 58 in elongated tube 52 through opening 62 in first end 60 thereof, FIG. 4. Terminal ends 31a and 33a of first and second barbs 31 and 33, respectively, are urged towards each other to facilitate insertion of capsule 12 into elongated tube 52. First end 72 of push rod 70 inserted through opening 62 in first end 60 of elongated tube 52 and engage first end 20 of capsule 12 so as to urge capsule 12 into passage 58 of elongated tube 52.

Once capsule 12 is positioned in elongated tube 52, second end 64 of elongated tube 52 is injected/inserted into a desired portion of a body, such as tumor 41. The beveled configuration of second end 64 of elongated tube 52 facilitates insertion of elongated tube 52 into tumor 41 to a desired depth. Thereafter, a user engages second end 74 of push rod 70 so as to urge push rod 70 axially into elongated tube 52 through opening 62 in first end 60 thereof. As push rod 70 is axially slid into elongated tube 52, first end 72 of push rod 70 engages second end 42 of capsule 12 and urges capsule 12 from the passage 58 of elongated tube 52 through output opening 66 thereof into tumor 41, FIGS. 5-6. As capsule 12 is urged from passage 58 of elongated tube 52 through output opening 66 thereof into tumor 41, first and second barbs 31 and 33, respectively, exit output opening 66 and are biased outwardly from delivery needle 26 into tumor 41, FIG. 6. First and second barbs 31 and 33, respectively, act to anchor capsule 12 in tumor 41 at the desired location in tumor 41.

Figure 7:
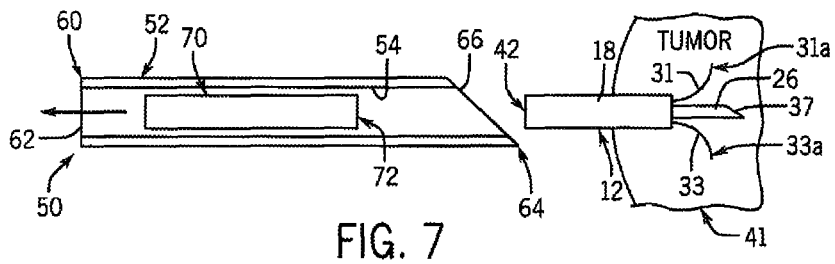
FIG. 7 is an enlarged, cross-sectional view showing the capsule of the microfluidic is device being retained in the tumor as the delivery instrument of the microfluidic device is removed from the tumor.

After capsule 12 is anchored in tumor 41, delivery instrument 50 is slid axially such that second end of elongated tube 52 is removed from tumor 41 while capsule 12 is retained therein, as previously described, FIG. 7. With capsule 12 anchored in tumor 41, the user selected compound in reservoir 18 diffuses into tumor 41 through output end 37 of delivery needle 26 so as to form a gradient of the user selected compound in tumor 41. Delivery needle 26 acts as a regulator to control diffusion of the user selected compound into tumor 41 at output end 37 of delivery needle 26 to insure that the user selected compound provided to tumor 41 is at a clinically relevant concentration. It can be appreciated that the concentration of the user selected compound at output end 37 of delivery needle 26 may be tailored by altering the dimensions of delivery needle 26 (e.g. by lengthening or shortening delivery needle 26 or increasing the cross sectional area thereof). Alternatively, the concentration of the user selected compound at output end 37 of delivery needle 26 may be tailored by changing the initial concentration of the user selected compound within reservoir 18.

As described, capsule 12 has the capability to maintain consistent delivery of the user selected compound for weeks, after which tumor 41 may be removed and sectioned to assess efficacy of the user selected compound. It is contemplated to conduct live imaging of tumor 41 during the delivery of the user selected compound to further assess the effect of the user selected compound. It can be appreciated that the total volume of the user selected compound within reservoir 18 is low enough that no systemic effects would be observed in the event of a device failure.

Figure 8:
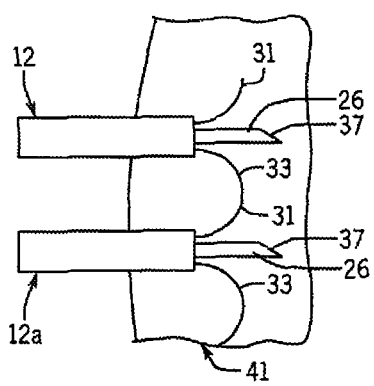
FIG. 8 is an enlarged, cross-sectional view showing first and second capsules being retained in the tumor.

After implantation of capsule 12 in tumor 41, as heretofore described, it is contemplated to inject additional capsules, e.g. capsule 12a, into tumor 41 to enable multiplexed assays, wherein clinicians can test either a single drug or multiple drugs in parallel, FIG. 8. More specifically, after implantation of capsule 12 in tumor 41, delivery instrument 50 may be subsequently loaded with a second capsule 12a having a second, user selected compound provided therein, in the manner previously described. Capsule 12a is identical in structure to capsule 12, but for the compound provided in reservoir 18.

Figure 9:
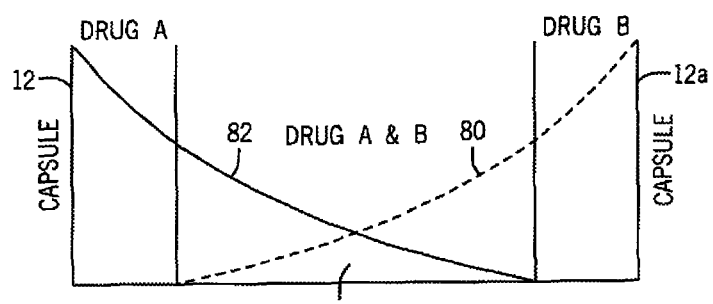
FIG. 9 is a graphical representation of the diffusion pattern of first and second drugs provided to the tumor by the first and second capsules, respectively, of FIG. 8.

Capsule 12a is injected into and anchored to tumor 41, as heretofore described, at a user desired location. With capsule 12a anchored in tumor 41, the second user selected compound diffuses from reservoir 18 into tumor 41 through output end 37 of delivery needle 26 so as to form gradient 80 of the second user selected compound (Drug B, FIG. 9) in tumor 41. By way of example, capsule 12a may be positioned such that a portion of gradient 80 of the second user selected compound (Drug B) in tumor 41 overlaps a portion of gradient 82 of the user selected compound (Drug A) in tumor 41 provided by capsule 12, FIG. 9. The intersection 84 of the gradients 80 and 82 allows for a clinician to test the efficacy of each compound individually or in parallel. It can be appreciated that microfluidic device 10 and the methodology herein described allows for a determination of the highest efficacy of an anticancer drug combination for a tumor prior to the removal of such tumor from the body. It is understood that additional capsules housing additional, user selected compounds, may be injected into tumor 41 to further facilitate a determination of the highest efficacy of an anticancer drug or drug combination for the tumor.

Various modes of carrying out the invention are contemplated as being within the scope of the following claims particularly pointing out and distinctly claiming the subject matter, which is regarded as the invention.

We claim:

1. A device for the administration of a compound in a body, comprising:
   a capsule having an inner surface defining a reservoir for receiving the compound therein;
   a diffusion regulator having an input communicating with the reservoir and an output receivable in the body, the diffusion regulator configured to control the diffusion of the compound from the reservoir into the body with the output of the diffusion regulator received in the body; and
   a resilient retention structure projecting from the capsule, the retention structure having a variable configuration;
   wherein the diffusion regulator includes a needle having a first end communicating with the reservoir and a second end receivable in the body and defining the output of the diffusion regulator.

2. The device of claim 1 wherein the capsule has opposite first and second ends and wherein the device further comprises a seal engageable with the first end of the capsule, the seal configured for preventing the compound from exiting the reservoir through the first end of the capsule.

3. The device of claim 1 wherein the capsule has opposite first and second ends and wherein the retention structure includes at least one barb projecting from the second end of the capsule, the at least one barb engageable with the body.

4. A device for the administration of a compound in a body, comprising:
   a capsule having an inner surface defining a reservoir for receiving the compound therein;
   a diffusion regulator having an input communicating with the reservoir and an output receivable in the body, the diffusion regulator configured to control the diffusion of the compound from the reservoir into the body with the output of the diffusion regulator received in the body;
   a resilient retention structure projecting from the capsule, the retention structure having a variable configuration; and
   a delivery instrument including:
      an elongated tube having an inner surface defining a passage for receiving the capsule therein, and first and second ends; and
      a push rod slideably received in the first end of the elongated tube, the push rod engageable with the capsule for urging the capsule from the passage of the elongated tube through the second end thereof.

5. The device of claim 4 wherein the second end of the elongated tube is beveled to facilitate the insertion of the elongated tube into the body.

6. A device for the administration of a compound in a body, comprising:
   a capsule having an inner surface defining a reservoir for receiving the compound therein;
   a diffusion regulator having an input communicating with the reservoir and an output receivable in the body, the diffusion regulator configured to control the diffusion of the compound from the reservoir into the body with the output of the diffusion regulator received in the body;
   a resilient retention structure projecting from the capsule, the retention structure having a variable configuration; and
   a delivery instrument configured for positioning the output of the diffusion regulator within the body, the delivery instrument including:
      a barrel having an interior adapted to receive the capsule therein; and
      a dispersal element configured to expel the capsule from the barrel.

7. A device for the administration of a compound in a body, comprising:
   a capsule having a reservoir therein for receiving the compound therein;
   a delivery instrument including:
      a barrel having an interior adapted to receive the capsule therein; and
      a dispersal element interacting with the capsule to selectively expel the capsule entirely from the barrel;
   a diffusion regulator having an input communicating with the reservoir and an output receivable in the body, the diffusion regulator controlling the diffusion of the compound from the reservoir into the body with the output of the diffusion regulator received in the body; and
   a retention structure projecting from the capsule, the retention structure configured to retain the output of the diffusion regulator in the body at a desired location.

8. The device of claim 7 wherein the capsule has opposite first and second ends and wherein the device further comprises a seal engageable with the first end of the capsule, the seal configured to prevent the compound from exiting the reservoir through the first end of the capsule.

9. The device of claim 7 wherein the diffusion regulator includes a needle having a first end communicating with the reservoir and a second end receivable in the body and defining the output of the diffusion regulator.

10. The device of claim 7, wherein the retention structure includes at least one barb projecting from the capsule, the at least one barb is movable from a first retracted position to a second extended position in response to the capsule being expelled from the barrel.

11. The device of claim 7 wherein the barrel is defined by an elongated tube having an inner surface defining a passage for receiving the capsule therein, and first and second ends.

12. The device of claim 11 wherein the dispersal element includes a push rod slideably received in the first end of the elongated tube, the push rod engageable with the capsule for selectively urging the capsule from the passage of the elongated tube through the second end thereof.

13. The device of claim 11 wherein the second end of the elongated tube is beveled to facilitate the insertion of the elongated tube into the body.

14. A device for the administration of a compound in a body, comprising:
   a capsule having a reservoir therein for receiving the compound therein;
   a diffusion regulator having an input communicating with the reservoir and an output receivable in the body, the diffusion regulator controlling the diffusion of the compound from the reservoir into the body with the output of the diffusion regulator received in the body; and a resilient retention structure projecting from the capsule and having a variable configuration, the retention structure configured to retain the capsule at a desired location with respect to the body with the output of the diffusion regulator received in the body;

an injection structure engageable with the capsule to selectively inject the output of the diffusion regulator into the body.

15. The device of claim 14 wherein the injection structure includes an elongated tube having an inner surface defining a passage for receiving the capsule therein, and first and second ends.

16. The device of claim 15 wherein the injection structure includes a push rod slideably received in the first end of the elongated tube, the push rod engageable with the capsule for selectively urging the capsule from the passage of the elongated tube through the second end thereof.

17. The device of claim 16 wherein the retention structure includes at least one barb projecting from the capsule, the at least one barb is movable from a first retracted position to a second extended position in response to ejection of the capsule from the passage of the elongated tube.

18. The device of claim 15 wherein the second end of the elongated tube is beveled to facilitate the insertion of the elongated tube into the body.

19. The device of claim 14 wherein the capsule has opposite first and second ends and wherein the device further comprises a seal engageable with the first end of the capsule, the seal configured to prevent the compound from exiting the reservoir through the first end of the capsule.

20. A device for the administration of a compound in a body, comprising:

a capsule having a reservoir therein for receiving the compound therein;

a diffusion regulator having input communicating with the reservoir and an output receivable in the body, the diffusion regulator controlling diffusion of the compound from the reservoir into the body with the output of the diffusion regulator received in the body; and a resilient retention structure projecting from the capsule and having a variable configuration, the retention structure configured to retain the capsule at a desired location with respect to the body with the output of the diffusion regulator received in the body; wherein the diffusion regulator includes a needle having a first end communicating with the reservoir and a second end receivable in the body.

* * * * *